United States Patent
Allef et al.

(10) Patent No.: US 7,906,664 B2
(45) Date of Patent: Mar. 15, 2011

(54) POLYGLYCEROL PARTIAL ESTERS OF POLYRICINOLEIC ACID AND POLYFUNCTIONAL CARBOXYLIC ACIDS AND THE USE THEREOF FOR PRODUCING EMULSIONS AND DISPERSIONS

(75) Inventors: Petra Allef, Bonn (DE); Wolfgang Berkels, Bottrop (DE); Hannelore Fötsch, Essen (DE); Jürgen Meyer, Muenster (DE)

(73) Assignee: Evonik Goldschmidt GmbH, Essen (DE)

( * ) Notice: Subject to any disclaimer, the term of this patent is extended or adjusted under 35 U.S.C. 154(b) by 938 days.

(21) Appl. No.: 11/335,250

(22) Filed: Jan. 19, 2006

(65) Prior Publication Data

US 2006/0165627 A1    Jul. 27, 2006

(30) Foreign Application Priority Data

Jan. 21, 2005 (DE) .......................... 10 2005 003 164

(51) Int. Cl.
C07C 51/00 (2006.01)
A61K 47/00 (2006.01)

(52) U.S. Cl. ........ 554/166; 554/124; 554/163; 554/227; 514/785; 514/772; 514/844; 514/937; 424/401

(58) Field of Classification Search .......... 516/22, 516/21, 33, 31, 63; 554/124, 166, 163, 227; 514/785, 937; 424/401

See application file for complete search history.

(56) References Cited

U.S. PATENT DOCUMENTS

| 2,482,761 A | 9/1949 | Goebel |
| 3,256,304 A | 6/1966 | Fischer et al. |
| 5,736,581 A * | 4/1998 | Ansmann et al. ............. 514/785 |
| 5,840,943 A * | 11/1998 | Ansmann et al. ............. 554/166 |
| 6,242,499 B1 * | 6/2001 | Gruning et al. ............. 514/785 |

FOREIGN PATENT DOCUMENTS

| DE | 37 40 186 A1 | 1/1989 |
| DE | 39 38 140 A1 | 8/1991 |
| DE | 42 38 081 A1 | 7/1993 |
| DE | 42 04 321 A1 | 8/1993 |
| DE | 42 29 707 A1 | 3/1994 |
| DE | 42 29 737 A1 | 3/1994 |
| DE | 43 09 372 A1 | 9/1994 |
| DE | 43 24 219 A1 | 1/1995 |
| DE | 44 09 569 C1 | 8/1995 |
| DE | 44 20 516 C2 | 10/1998 |
| DE | 198 55 934 A1 | 6/2000 |
| EP | 0 835 862 B1 | 3/2001 |
| WO | WO 94/09753 | 5/1994 |

OTHER PUBLICATIONS

Finkel, P. "Formulierung Kosmetischer Sonnenschutzmittel." *SÖFW J.* No. 122 p. 543-548 (1996).

* cited by examiner

*Primary Examiner* — Porfirio Nazario Gonzalez
*Assistant Examiner* — Yate K Cutliff
(74) *Attorney, Agent, or Firm* — Scully, Scott, Murphy & Presser, P.C.

(57) ABSTRACT

The invention relates to polyglycerol partial esters of polyricinoleic acid and polyfunctional carboxylic acids, obtainable by esterification of a a) polyglycerol mixture with
b) at least one polyricinoleic acid and
c) at least one di- and/or tricarboxylic acid and optionally
d) at least one fatty acid having 6 to 22 carbon atoms by methods known per se, and to the use thereof for producing cosmetic or pharmaceutical emulsions or dispersions.

9 Claims, No Drawings

POLYGLYCEROL PARTIAL ESTERS OF POLYRICINOLEIC ACID AND POLYFUNCTIONAL CARBOXYLIC ACIDS AND THE USE THEREOF FOR PRODUCING EMULSIONS AND DISPERSIONS

FIELD OF THE INVENTION

The present invention relates to polyglycerol partial esters of polyricinoleic acid and polyfunctional carboxylic acids, which are obtainable by esterification of a polyglycerol mixture comprising polyricinoleic acid with aliphatic, linear or branched dicarboxylic acids having a chain length of from 2 to 36 carbon atoms and saturated or unsaturated, linear or branched fatty acids having 6 to 22 carbon atoms, where the degree of esterification of the polyglycerol mixture is between 20 and 75%. The present invention also relates to the use of the aforementioned polyglycerol partial esters for producing emulsions and dispersions for, in particular, cosmetic and pharmaceutical formulations.

BACKGROUND OF THE INVENTION

It is known to one skilled in the art that water-in-oil emulsions are difficult to stabilize against coalescence of water droplets and thus against water separation due to the tight packing of the water droplets, which is a consequence of the usually high proportion of disperse phase (>65%). A further consequence of the high packing density is a per se high viscosity of the emulsion.

In order to achieve a stability required by the cosmetic industry, stabilizing waxes and sometimes also high-viscosity oils are generally used, both of which increase the viscosity of the (external) oil phase, thus reducing the mobility of the water droplets and protecting against coalescence. High-viscosity oils and stabilizing waxes, however, have an adverse effect on the feel on the skin; in particular, these types of oils and waxes induce a heavy and sticky feeling on the skin. Although, in principle, it is possible to switch to oil-in-water emulsions, which, as is known, have a lighter feel on the skin, as alternatives, these types of emulsions have a significantly lower care effect than oil-in-water emulsions.

It is thus a generally desirable aim to make water-in-oil emulsions as light as possible, i.e., low viscosity, like oil-in-water emulsions, without having to sacrifice their particular care effect. In particular, one object is to permit water-in-oil emulsions to have the lowest possible viscosity, which are nonsticky and nevertheless stable. A particular challenge in this area is the formulation of oil-in-water emulsions which are of such low viscosity that they are sprayable. In this connection, the emulsifier to be used plays a particular key role.

W/O (water-in-oil) emulsifiers which are based on natural raw materials are of considerable interest for ecological reasons both to manufacturers and also to the consumers of emulsion preparations. These are, in particular, emulsifiers which contain no polyethylene glycol-containing radicals ("PEG-free" emulsifiers). For this reason, and despite their often average performance, partial esters of polyalcohols, such as glycerol, polyglycerol, sorbitol or methyl glycoside, and fatty acids, such as oleic acid or isostearic acid, continue to be used widely.

This type of emulsifier is not suitable, for example, for flowable emulsions (lotions) and for creams with a high content of natural triglycerides. The creams corresponding to the stability requirements of the market (thermal stability from −15° to +45° C., sometimes from −25° to +50° C.) consist of lipid-like components, predominantly paraffin oils and fatty acid esters of monoalkanols (MW<500); these have more favorable technological properties than the higher molecular weight triglycerides. Nevertheless, for stabilization, relatively high concentrations of viscosity-increasing waxes ($\geq$3%) are required; however these have an adverse effect on the application properties since they produce an undesired sticky-greasy feel on the skin.

The polyglycerol esters of di- and polymerized unsaturated $C_{18}$-fatty acids have considerably better emulsification properties than the polyalcohol fatty acid partial esters. These polyglycerol esters are obtained from the mono- and diglycerides of vegetable oils, preferably soya oil, by thermal treatment for a number of hours at about 300° C. or by the transesterification of a thermally polymerized vegetable oil with polyglycerol.

The polyglycerol polyricinoleates formed by an analogous method from castor oil are likewise high-performance W/O emulsifiers (see, for example, DE-B-44 09 569).

On account of their sensitivity to oxidation and the sometimes marked greasy-rancid odor, this class of substance has hitherto only become established in a few cosmetic or pharmaceutical emulsion preparations. The massive thermal stress during production and the unsaturated character (e.g., iodine number about 100) are primarily responsible for this.

Polyglycerol polyhydroxystearate, which is chemically related to polyglycerol polyricinoleate and can likewise be prepared from vegetable raw materials, is likewise used as a W/O emulsifier. Polyglycerol polyhydroxystearates have a higher oxidation stability and thus an increased sensory quality (see, for example, DE-C-44 20 516).

However, both classes of substances are only able to form relatively low-viscosity W/O lotions with an oil phase content of >22% by weight. On account of this minimum amount of oil phase and on account of the rather rich sensory character of these emulsions, the formulation of stable W/O emulsions with a very light feel on the skin is not possible or is only possible to a very limited degree. Added to this is the fact that emulsifiers of this type, particularly when formulating triglyceride-containing formulations, often have problems with low-temperature stability, which in many cases can only be solved by adding coemulsifiers.

The improvement in the freeze-thaw stability is of considerable practical interest for the transportability and storability of emulsion preparations. As a result of prolonged storage at very low temperatures, or as a result of extreme temperature fluctuations during extended transportation, the inadequate emulsion stabilization can become apparent from significant water separations in emulsion preparation or even lead to the complete breaking of the emulsion.

EP-B-0 835 862 describes polyglycerol partial esters obtainable by esterification of a polyglycerol mixture with a degree of esterification of the polyglycerol between 30 and 75% and saturated or unsaturated, linear or branched fatty acids having 12 to 22 carbon atoms and dimer fatty acids with an average functionality of from 2 to 2.4. These esters have an additional advantage over polyglycerol polyhydroxystearate in that the freeze stability of emulsions containing the polyglycerol partial esters is significantly improved. However, the emulsions are still relatively thick, for which reason these polyglycerol partial esters are primarily suitable for producing rich lotions and creams.

An object of the present invention is therefore to develop a PEG-free emulsifier which permits the formulation of low-viscosity emulsions that have a pleasantly light feel on the skin and at the same time the required freeze-thaw stability.

SUMMARY OF THE INVENTION

Surprisingly, it has now been found that very low-viscosity, light water-in-oil emulsions can be obtained using emulsifiers based on polyglycerol partial esters of polyricinoleic acid which are additionally linked via di- or tricarboxylic acids. These linked polyglycerol polyricinoleates have neither a greasy-rancid odor, nor do they exhibit a greater sensitivity to oxidation than polyglycerol polyhydroxystearates. Using the inventive emulsifiers it is possible, in contrast to uncrosslinked polyglyceryl ricinoleates and polyhydroxystearates, to formulate emulsions with considerably lower viscosity. This makes it possible to formulate lotions with a very low oil phase content (<22% by weight) which have a correspondingly light feel on the skin.

The present invention therefore provides polyesters of polyricinoleic acid and polyfunctional carboxylic acids, obtainable by esterification of
a) a polyglycerol mixture with
b) at least one polyricinoleic acid of the general formula 1

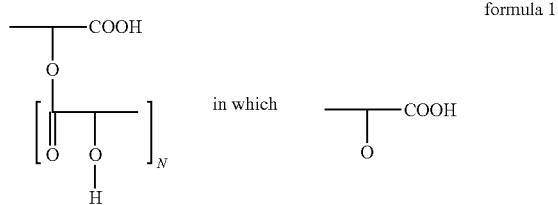

formula 1 in which is the radical of ricinoleic acid $CH_3$—$(CH_2)_5$—$CH(OH)$—$CH_2$—$CH=CH$—$(CH_2)_7$—$COOH$ and optionally of hydroxystearic acid $CH_3$—$(CH_2)_5$—$CH(OH)$—$(CH_2)_{10}$—$COOH$, where the homopolymers are preferably based on ricinoleic acid, N is 1 to 10, preferably 2 to 8, in particular 2 to 5, and optionally b1) polyhydroxystearic acid, and c) at least one di- and/or tricarboxylic acid and d) at least one fatty acid having 6 to 22 carbon atoms by methods known per se.

The invention further provides polyesters of polyricinoleic acid and polyfunctional carboxylic acids, obtainable by esterification a) of a polyglycerol mixture with b) at least one polyricinoleic acid of the general formula 1

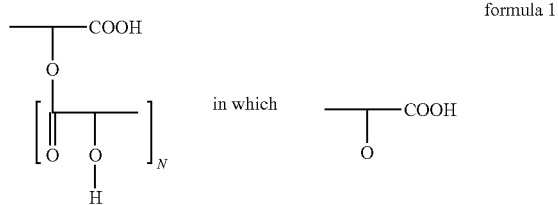

formula 1 in which is the radical of ricinoleic acid $CH_3$—$(CH_2)_5$—$CH(OH)$—$CH_2$—$CH=CH$—$(CH_2)_7$—$COOH$ and optionally of hydroxystearic acid $CH_3$—$(CH_2)_5$—$CH(OH)$—$(CH_2)_{10}$—$COOH$, where the homopolymers are preferably based on ricinoleic acid, N is 1 to 10, preferably 2 to 8, in particular 2 to 5, and optionally b1) polyhydroxystearic acid, and c) at least one di- and/or tricarboxylic acid by methods known per se.

The present invention further provides polyglycerol partial esters as disclosed herein, prepared by esterification of a) 1.0 mol of OH groups of the polyglycerol mixture with b) 0.01 to 0.5 mol, in particular 0.05 to 0.3 mol, of COOH groups of the polyricinoleic acid, and c) 0.01 to 0.5 mol, in particular 0.05 to 0.3 mol, of COOH groups of at least one di- and/or tricarboxylic acid, and d) 0.01 to 0.9 mol, in particular 0.1 to 0.6 mol, of COOH groups of the fatty acids having 6 to 22 carbon atoms, with the proviso that the sum of the COOH groups corresponds to about 20 to 75% of the OH groups of the polyglycerol mixture.

The present invention further provides cosmetic, dermatological or pharmaceutical preparations which comprise at least one of the polyglycerol partial esters according to the instant invention. These preparations are preferably emulsions which can optionally comprise dispersed solids. In particular, the use of the polyglycerol partial esters according to the invention as water-in-oil emulsifiers or dispersion auxiliaries is at the forefront here.

The invention further provides care and cleaning compositions for household and industry, in particular for hard surfaces, for leather or textiles, which comprise at least one of the polyglycerol partial esters according to the present invention. These preparations are preferably emulsions which can optionally comprise dispersed solids. In particular, the use of the polyglycerol partial esters as water-in-oil emulsifiers or dispersion auxiliaries is at the forefront here.

DETAILED DESCRIPTION OF THE INVENTION

The present invention, which relates to polyglycerol partial esters of polyricinoleic acid and polyfunctional carboxylic acids, will now be described in greater detail by referring to the following discussion.

Before discussing the invention in detail, it is noted that the condensation products based on ricinoleic acid according to the present invention are liquid and are thus also suitable for the energy-saving "cold-cold" preparation of emulsions besides the classic "hot-hot" preparation.

The polyricinoleic acids co-used according to the invention are prepared in accordance with the known methods of the prior art, for example, by polycondensation of ricinoleic acid, optionally with co-use of hydroxystearic acid.

Esterification products of the general formula 1

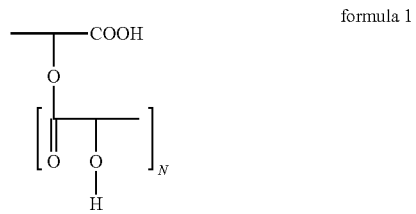

formula 1 where
N forms 1 to 10, preferably 2 to 8, in particular 2 to 5, fatty acid units which have acid numbers between 187 and 20, preferably between 96 and 45, and in which
the radical

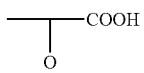

is preferably only the radical of ricinoleic acid $CH_3$—$(CH_2)_5$—$CH(OH)$—$CH_2$—$CH$=$CH$—$(CH_2)_7$—$COOH$,
are prepared.

According to the present invention, it is also possible to use mixtures of polyricinoleic acid and polyhydroxystearic acid.

Suitable polyglycerols are, in particular, those of the general formulae 2A and 2B

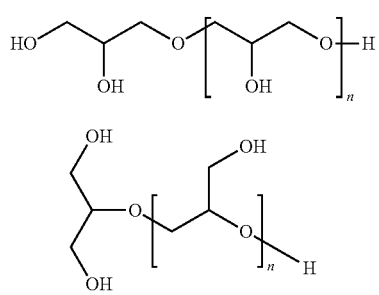

formula 2A formula 2B with an average degree of condensation n of from 1 to 11, preferably 2 to 6 and hydroxyl numbers from about 1350 to about 800, preferably about 1200 to about 900. The polyglycerol mixtures can also comprise other regioisomers or cycles.

These are technical-grade polyglycerol mixtures which are obtained, for example, by alkali-catalyzed condensation of glycerol at elevated temperatures, from which it is possible to obtain fractions with the desired degree of condensation, if appropriate, through distillation processes. Likewise, of suitability, are also polyglycerols which are obtained in another way, e.g., from epichlorohydrin or glycidol.

It has proven particularly advantageous to use polyglycerols which have the following homolog distribution (GC method); the preferred ranges are given in brackets:
Glycerol: 0 to 20 (<5) % by weight
Diglycerols: 0 to 60 (5 to 30) % by weight
Triglycerols: 0 to 60 (5 to 50) % by weight
Tetraglycerols: 0 to 30 (5 to 25) % by weight
Pentaglycerols: 0 to 30 (5 to 20) % by weight
Oligoglycerols: ad 100% by weight Of particular suitability for the intended use according to the present invention, as emulsifiers, is the use of relatively short-chain di- or tricarboxylic acids, such as, oxalic acid, malonic acid, succinic acid, glutaric acid, adipic acid, pimelic acid, suberic acid, azelaic acid, sebacic acid, or dodecanedioic acid. Hydroxydi- and tricarboxylic acids, such as, malic acid, tartaric acid, or citric acid, are likewise suitable. Furthermore, aromatic acids, such as, phthalic acid, isophthalic acid or terephthalic acid, can be used.

The dimeric fatty acids optionally co-used to prepare the compounds according to the present invention are standard commercial products which are prepared by polymerization of saturated or unsaturated natural or synthetic monobasic aliphatic fatty acids having 16 to 22 carbon atoms in accordance with known methods (see, for example, U.S. Pat. No. 2,482,761, and U.S. Pat. No. 3,256,304). Typical commercially available dimeric fatty acids have, for example, the following composition:

| monomeric acids | 0 to 15% by weight |
|---|---|
| dimeric acids | 60 to 95% by weight |
| tri- and higher polymerized acids | 1 to 35% by weight | where the content can fluctuate within these limits depending on the origin of the monomers, the polymerization process and the work-up process.

The dimeric fatty acid used may also be present in hydrogenated form.

The content of dimeric acid can be increased to 100% by weight by generally known distillation processes. It is determined by the known processes of gas-liquid chromatography (GLC). The acid numbers are in the range from about 190 to 200.

By co-using these acids, a significantly improved stabilization of the phase interfaces in W/O emulsions can be achieved.

Suitable additional fatty acid components are primarily saturated fatty acids, such as, for example, lauric acid, tridecanoic acid, myristic acid, palmitic acid, margaric acid, stearic acid, isostearic acid, arachidic acid and behenic acid, and mixtures thereof.

Naturally occurring mixtures are, for example, the coconut fatty acids which comprise, as a main constituent, lauric acid, and also saturated $C_{14}$-$C_{18}$-fatty acids and optionally saturated $C_8$-$C_{10}$-fatty acids and unsaturated fatty acids, and also tallow fatty acids, which essentially constitute a mixture of palmitic acid and stearic acid.

Suitable additional unsaturated fatty acid components are monoolefinically unsaturated acids, for example, hexadecenoic acids, octadecenoic acids, such as, oleic acid (cis-9-octadecenoic acid) or elaidic acid (trans-9-octadecenoic acid), eicosenoic acids and docosenoic acids, such as, erucic acid (cis-13-docosenoic acid) or brassidic acid (trans-13-docosenoic acid), polyunsaturated fatty acids, for example, octodecadienoic acids and octodecatrienoic acids, such as, linoleic acid and linolenic acid, and mixtures thereof.

Of particular suitability are the liquid fatty acids, such as, oleic acid, ricinoleic acid, erucic acid and isostearic acid which contain 18 to 22 carbon atoms. On account of branching or a double bond in the hydrocarbon chain, their solidification points are below 35° C. It is also possible to use fatty acid mixtures, which may also comprise wax-like components, such as, hydrogenated ricinoleic acid.

Furthermore, the use of lactones, such as, butyrolactone or caprolactone, as fatty acid component is possible.

In the polyglycerol partial esters according to the instant invention, the hydroxyl groups of the polyglycerol are esterified to 20 to 75%, preferably 40 to 70%.

For their preparation, preference is given to the variants A) and B) according to which in
A) the first stage polyglycerol is esterified to a degree of esterification of from 10 to 70%, preferably 25 to 40%, with fatty acid and dicarboxylic acid and/or tricarboxylic acid, and then in a second stage is esterified with polyricinoleic acid to a total degree of esterification of from 20 to 75%, preferably 40 to 60%, or in B) the first stage polyglycerol is esterified to a degree of esterification of from 10 to 70%, preferably 25 to 40%, with fatty acid and polyricinoleic acid and in a second stage is esterified with dicarboxylic acid and/or tricarboxylic acid to a total degree of esterification of from 20 to 75%, preferably 40 to 60%.

Adding the components in another order, such as, for example, adding firstly the fatty acid, then the dicarboxylic acid and/or tricarboxylic acid and subsequently the polyricinoleic acid, and one-pot processes are likewise possible.

Through appropriate choice of the hydrophilic and lipophilic molecular moieties it is possible, for example, to establish an HLB value of from about 3 to 8 in order to obtain properties which are favorable for the stabilization of W/O emulsions.

The polyglycerol partial esters according to the present invention can be prepared in a manner known per se by heating the reaction components to 100° to 300° C., preferably 180° to 260° C., and removing the water of reaction which forms by distillation. To increase the rate, acidic or basic catalysts, such as, sulfonic acids, phosphoric acid or phosphorous acid, Lewis acids, such as, zinc salts, alkali metal or alkaline earth metal oxides or hydroxides, alkoxides or salts, can be co-used. The addition of a catalyst, however, is not absolutely necessary. The progressing conversion can be monitored, for example, by means of the water of reaction which has been separated off, by measuring the acid number or by infrared spectroscopy. In general, an acid number in the end product of <20, preferably <10, is the aim. Particular preference is given to products with an acid number of <5.

The polyglycerol esters according to the present invention are particularly suitable for producing emulsions and dispersions in which the oil phase is the external phase.

Under certain prerequisites, e.g., by adding suitable hydrophilic co-emulsifiers, the polyglycerol esters according to the present invention can also be used for producing emulsions and dispersions in which the aqueous phase forms the external phase.

Preference is given to their use as emulsifiers and dispersion auxiliaries for producing cosmetic or pharmaceutical preparations. These are cosmetic preparations which, through the use of oil-in-water or water-in-oil emulsifiers, are given a readily spreadable consistency because these emulsifier systems allow an oil or a fat to be readily incorporated into an aqueous phase, or an aqueous phase to be readily incorporated into an oil or a fat, for example, creams, such as, care creams, baby creams or sun protection creams, ointments, lotions or make-up. In pharmaceutical preparations, such as, ointments or creams, oil-in-water or water-in-oil emulsifiers are required for the formulation of active ingredients.

The cosmetic oils which are co-used include, in particular, mono- or diesters of linear and/or branched mono- and/or dicarboxylic acids having 2 to 44 carbon atoms with linear and/or branched saturated or unsaturated alcohols having 1 to 22 carbon atoms. Likewise of suitability within the meaning according to the present invention are the esterification products of aliphatic, difunctional alcohols having 2 to 36 carbon atoms with monofunctional aliphatic carboxylic acids having 1 to 22 carbon atoms. Monoesters suitable as oil components are, for example, the methyl esters and isopropyl esters of fatty acids having 12 to 22 carbon atoms, for example, methyl laurate, methyl stearate, methyl oleate, methyl erucate, isopropyl palmitate, isopropyl myristate, isopropyl stearate, or isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, or erucyl oleate, and esters which are obtainable from technical-grade aliphatic alcohol cuts and technical-grade, aliphatic carboxylic acid mixtures, e.g., esters of unsaturated fatty alcohols having 12 to 22 carbon atoms and saturated and unsaturated fatty acids having 12 to 22 carbon atoms, as are obtainable from animal and vegetable fats. Also of suitability, however, are naturally occurring monoester and/or wax ester mixtures, as are present, for example, in jojoba oil or in sperm oil.

Examples of dicarboxylic acid esters which are co-used include di-n-butyl adipate, di-n-butyl sebacate, di(2-ethylhexyl) adipate, or di(2-hexyldecyl) succinate, diisotridecyl acelate. Suitable diol esters are, for example, ethylene glycol dioleate, ethylene glycol diisotridecanoate, propylene glycol di(2-ethylhexanoate), butanediol diisostearate and neopentyl glycol dicaprylate.

Further fatty acid esters which can be used are, for example, $C_{12-15}$-alkyl benzoate, dicaprylyl carbonate, or diethylhexyl carbonate.

As oil component it is likewise possible to use fatty acid triglycerides, preference being given among these to the naturally occurring oils and fats. Thus, for example, natural vegetable oils, e.g., olive oil, sunflower oil, soya oil, peanut oil, rapeseed oil, almond oil, palm oil, but also the liquid fractions of coconut oil or of palm kernel oil, and animal oils, such as, for example, neatsfoot oil, the liquid fractions of beef tallow or also synthetic triglycerides of caprylic/capric acid mixtures, triglycerides of technical-grade oleic acid or of palmitic acid/oleic acid mixtures are suitable as oil components.

In addition, hydrocarbons, in particular liquid paraffins and isoparaffins, can be used. Examples of hydrocarbons which can be used are paraffin oil, isohexadecane, polydecene, vaseline, paraffinum perliquidum, or squalane.

In addition, it is also possible to use linear or branched fatty alcohols, such as, oleyl alcohol or octyldodecanol, and fatty alcohol ethers, such as, dicaprylyl ether.

Suitable silicone oils and silicone waxes are, for example, polydimethylsiloxanes, cyclomethylsiloxanes, and also aryl- or alkyl- or alkoxy-substituted polymethylsiloxanes or cyclomethylsiloxanes.

In addition, auxiliaries and additives customary in cosmetic and pharmaceutical applications and known to the person skilled in the art can be used. These include, for example, co-emulsifiers, consistency regulators, thickeners, waxes, UV photoprotective filters, antioxidants, hydrotropes, deodorant and antiperspirant active ingredients, insect repellents, self-tanning agents, preservatives, perfume oils, dyes and biogenic active ingredients.

Besides the polyglycerol esters according to the present invention, additional emulsifiers or surfactants can also be used. These are preferably nonionic, anionic, cationic or amphoteric surfactants.

In particular, the polyglycerol esters according to the present invention can be used in W/O emulsions, which can additionally also comprise dispersed solids, for keeping the overall viscosity of the preparation as low as possible.

Non-ionogenic emulsifiers or surfactants which may be co-used are compounds from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group $C_{12/18}$-fatty acid mono- and diesters of addition products of from 1 to 30 mol of ethylene oxide onto glycerol glycerol mono- and diesters and sorbitan mono- and diesters of saturated and unsaturated fatty acids having 6 to 22 carbon atoms and ethylene oxide addition products thereof alkyl mono- and oligoglycosides having 8 to 22 carbon atoms in the alkyl radical and ethylene oxide addition products thereof addition products of from 2 to 200 mol of ethylene oxide onto castor oil and/or hydrogenated castor oil partial esters based on linear, branched, unsaturated or saturated $C_{6-22}$-fatty acids, ricinoleic acid, and 12-hydroxystearic acid and glycerol, polyglycerol, pentaerythritol, dipentaerythritol, sugar alcohols (e.g., sorbitol), alkyl glucosides (e.g., methyl glucoside, butyl glucoside, lauryl glucoside), and polyglucosides (e.g., cellulose).

Here, the use of partial esters of glycerol and of polyglycerol is preferred. These are, for example, glycerol oleate, glycerol isostearate, polyglycerol isostearates, polyglycerol oleates, polyglycerol polyricinoleates, polyglycerol poly-12-hydroxystearates or distearoyl polyglyceryl-3 dimer dilinoleate (ISOLAN® PDI, Degussa). Particularly in combination with distearoyl polyglyceryl-3 dimer dilinoleate (ISOLAN® PDI, Degussa), the polyglycerol partial esters according to the present invention can be used, depending on the mixing ratio of these two types of emulsifier, such that it is possible to obtain either low-viscosity water-in-oil lotions, or rich water-in-oil creams.

mono-, di- and trialkyl phosphates, and mono-, di- and/or tri-PEG alkyl phosphates and salts thereof polysiloxane-polyether copolymers (dimethicone copolyols), such as, for example, PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 14/12 or 20/20 or 18/18 or 17/18 or 15/15. Of particular suitability here are products such as bis-PEG/PPG-14/14 dimethicone (with cyclopentasiloxane: ABIL® EM 97 (Degussa)) or PEG/PPG-16/16 PEG/PPG-16/16 dimethicone (with caprylic/capric triglycerides: ABIL® Care 85 (Degussa))

polysiloxane-polyalkyl-polyether copolymers and corresponding derivatives, such as, for example, lauryl or cetyl dimethicone copolyols, in particular cetyl PEG/PPG-10/1 dimethicone (ABIL® EM 90 (Degussa))

mixed esters of pentaerythritol, fatty acids, citric acid and fatty alcohol according to DE-11 65 574 and/or mixed esters of fatty acids having 6 to 22 carbon atoms, methylglucose and polyols, preferably glycerol or polyglycerol.

It is also possible to additionally use anionic emulsifiers or surfactants.

These contain solubilizing anionic groups, such as, for example, a carboxylate, sulfate, sulfonate, or phosphate group and a lipophilic radical. Skin-compatible anionic surfactants are known to the person skilled in the art in large numbers and are commercially available. These are, in particular, alkyl sulfates or alkyl phosphates in the form of their alkali metal, ammonium or alkali ammonium salts, alkyl ether sulfates, alkyl ether carboxylates, acyl sarcosinates, and sulfosuccinates and acyl glutamates in the form of their alkali metal or ammonium salts.

Cationic emulsifiers can also be added as surfactants.

As such, it is possible to use, in particular, quaternary ammonium compounds, such as, alkyltrimethylammonium halides, such as, for example, cetyltrimethylammonium chloride or bromide or behenyltrimethylammonium chloride, but also dialkyldimethylammonium halides, such as, for example, disteraryldimethylammonium chloride. In addition, monoalkylamidoquats, such as, for example, palmitamidopropyltrimethylammonium chloride or corresponding dialkylamidoquats can be used. Furthermore, it is also possible to use readily biodegradable quaternary ester compounds, which are mostly quaternized fatty acid esters based on mono-, di- or triethanolamine. In addition, alkylguanidinium salts can be added as cationic emulsifiers.

In addition, it is possible to use amphoteric surfactants, such as, for example, betaines, amphoacetates or amphopropionates together with the polyglycerol esters according to the present invention.

In addition, the low-viscosity emulsions according to the present invention can comprise customary auxiliaries and additives, such as, thickeners, UV photoprotective filters, antioxidants, hydrotropes, deodorant and antiperspirant active ingredients, insect repellents, self-tanning agents, perfume oils, dyes and biogenic active ingredients.

Of suitability for thickening oil phases are all thickeners known to the person skilled in the art. Mention is made here in particular of waxes, such as, hydrogenated castor wax, beeswax or microwax. In addition, inorganic thickeners can also be used, such as, silica, alumina or sheet silicates (e.g., hectorite, laponite, saponite). These inorganic oil phase thickeners are here preferably hydrophobically modified.

For thickening/stabilizing water-in-oil emulsions prepared by a cold process, it is possible to use, in particular, aerosils and/or metal salts of fatty acids, such as, for example, zinc stearate.

UV photoprotective filters are understood as meaning organic substances which are able to absorb ultraviolet rays and release the absorbed energy again in the form of longer-wave radiation, e.g., heat. UV-B filters may be oil-soluble or water-soluble. Examples of oil-soluble substances are:

3-benzylidenecamphor and derivatives thereof, e.g., 3-(4-methylbenzylidene)camphor 4-aminobenzoic acid derivatives, preferably 2-ethylhexyl 4-(dimethylamino)benzoate, 2-ethylhexyl 4-(dimethylamino)benzoate and amyl 4-(dimethylamino)benzoate esters of cinnamic acid, preferably 2-ethylhexyl 4-methoxycinnamate, isopentyl 4-methoxycinnamate, 2-ethylhexyl 2-cyano-3-phenylcinnamate (octocrylene)

esters of salicylic acid, preferably 2-ethylhexyl salicylate, 4-isopropylbenzyl salicylate, homomenthyl salicylate derivatives of benzophenone, preferably 2-hydroxy-4-methoxybenzophenone, 2-hydroxy-4-methoxy-4'-methylbenzophenone, 2,2'-dihydroxy-4-methoxybenzophenone esters of benzalmalonic acid, preferably di-2-ethylhexyl 4-methoxybenzalmalonate triazine derivatives, such as, for example, 2,4,6-trianilino (p-carbo-2'-ethyl-1'-hexyloxy)-1,3,5-triazine and octyltriazone propane-1,3-diones, such as, for example, 1-(4-tert-butylphenyl)-3-(4'-methoxyphenyl)propane-1,3-dione.

Water-soluble substances which can be co-used are:

2-phenylbenzimidazole-5-sulfonic acid and the alkali metal, alkaline earth metal, ammonium, alkylammonium, alkanolammonium and glucammonium salts thereof sulfonic acid derivatives of benzophenone, preferably 2-hydroxy-4-methoxybenzophenone-5-sulfonic acid and its salts sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures. Besides the specified soluble substances, insoluble pigments are also suitable for this purpose, namely finely disperse metal oxides or salts, such as, for example, titanium dioxide, zinc oxide, iron oxide, aluminum oxide, cerium oxide, zirconium oxide, silicates (talc), barium sulfate and zinc stearate. The particles here should have an average diameter of less than 100 nm, preferably between 5 and 50 nm and in particular between 15 and 30 nm. They can have a spherical shape, although it is also possible to use particles which have an ellipsoidal shape or a shape which deviates in some other way from the spherical configuration. A relatively new class of photoprotective filters are micronized organic pigments, such as, for example, 2,2'-methylenebis{6-(2H-benzotriazol-2-yl)-4-(1,1,3,3-tetramethylbutyl)phenol} with a particle size of less than 200 nm, which is obtainable, for example, as 50% strength aqueous dispersion.

Besides the two abovementioned groups of primary photoprotective substances, it is also possible to use secondary photoprotective agents of the antioxidant type; these interrupt the photochemical reaction chain which is triggered when UV radiation penetrates into the skin. Typical examples thereof are superoxide dismutase, tocopherols (vitamin E) and ascorbic acid (vitamin C). Further suitable UV photoprotective filters can be found in the overview by P. Finkel in SÖFW-Journal 122, 543 (1996).

To improve the flow behavior and the application properties, it is also possible to use hydrotropes, such as, for example, ethanol, isopropyl alcohol, or polyols. Polyols which are suitable here preferably have 2 to 15 carbon atoms and at least two hydroxyl groups. Typical examples are glycerol alkylene glycols, such as, for example, ethylene glycol, diethylene glycol, propylene glycol, butylene glycol, hexylene glycol, and polyethylene glycols with an average molecular weight of from 100 to 1000 Daltons technical-grade oligoglycerol mixtures with a degree of self-condensation of from 1.5 to 10, such as, for example, technical-grade diglycerol mixtures with a diglycerol content of from 40 to 50% by weight methylol compounds, such as, in particular, trimethylolethane, trimethylolpropane, trimethylolbutane, pentaerythritol and dipentaerythritol lower alkyl glucosides, in particular those having 1 to 4 carbon atoms in the alkyl radical, such as, for example, methyl glucoside and butyl glucoside sugar alcohols having 5 to 12 carbon atoms, such as, for example, sorbitol or mannitol sugars having 5 to 12 carbon atoms, such as, for example, glucose or sucrose amino sugars, such as, for example, glucamine.

Suitable deodorant active ingredients are, for example, odor concealers, such as, the customary perfume constituents, odor absorbers, for example, the sheet silicates described in the patent laid-open specification DE-40 09 347, of these, in particular, montmorillonite, kaolinite, illite, beidelite, nontronite, saponite, hectorite, bentonite, or smectite, also, for example, zinc salts of ricinoleic acid. Antibacterial agents are likewise suitable for incorporation into the oil-in-water emulsions according to the invention. Advantageous substances are, for example, 2,4,4'-trichloro-2'-hydroxydiphenyl ether (irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), ethylhexyl glyceryl ether, polyglyceryl-3 caprylate (TEGO® Cosmo P813, Degussa), and the active agents described in the patent laid-open specifications DE-198 55 934, DE-37 40 186, DE-39 38 140, DE-42 04 321, DE-42 29 707, DE-42 29 737, DE-42 38 081, DE-43 09 372, DE-43 24 219 and EP-666 732. Further customary antiperspirant active ingredients can likewise be used advantageously in the preparations according to the present invention, in particular astringents, for example, basic aluminum chlorides, such as aluminum chlorohydrate ("ACH") and aluminum zirconium glycine salts ("ZAG").

Suitable insect repellents are N,N-diethyl-m-toluamide, 1,2-pentanediol or Insect Repellent 3535.

Suitable self-tanning agents are, for example, dihydroxyacetone and erythrulose.

Suitable preservatives which may be used are, for example, mixtures of one or more alkyl paraben esters with phenoxyethanol. The alkyl paraben esters are preferably methyl paraben, ethyl paraben, propyl paraben and/or butyl paraben. Instead of phenoxyethanol it is also possible to use other alcohols, such as, for example, benzyl alcohol or ethanol. Moreover, it is also possible to use other customary preservatives, such as, for example, sorbic acid or benzoic acid, salicylic acid, 2-bromo-2-nitropropane-1,3-diol, chloroacetamide, diazolidinylurea, DMDM hydantoin, iodopropynyl butylcarbamate, sodium hydroxymethyl-glycinate or the combination chloromethyl-/methylisothiazoline.

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (anis, coriander, caraway, juniper), fruit peels (bergamot, lemons, oranges), roots (mace, angelica, celery, cardamom, costus, iris, thyme), needles and branches (spruce, fir, pine, dwarf-pine), resins and balsams (galbanum, elemi, benzoin, myrrh, olibanum, opoponax). Animal raw materials are also suitable, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butyl cyclohexylacetate, linalyl acetate, dimethylbenzylcarbinyl acetate, phenylethyl acetate, linalyl benzoate, benzyl formate, ethylmethyl phenylglycinate, allyl cyclohexylpropionate, styrallyl propionate and benzyl salicylate. The ethers include, for example, benzyl ethyl ether, the aldehydes include for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethol, citronellol, eugenol, isoeugenol, geraniol, linalool, phenylethyl alcohol and terpineol, and the hydrocarbons include primarily the terpenes and balsams. However, preference is given to using mixtures of different fragrances which together produce a pleasing scent note. Essential oils of low volatility, which are mostly used as aroma components, are also suitable as perfume oils, e.g., sage oil, chamomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, vertofix coeur, iso-E-super, fixolide NP, evernyl, iraldein gamma, phenylacetic acid, geranyl acetate, benzyl acetate, rose oxide, romillat, irotyl and floramat alone or in mixtures.

Dyes which can be used are the substances which are approved and suitable for cosmetic purposes, as are listed, for example, in the publication "Kosmetische Färbemittel" [Cosmetic colorants] from the Dyes Commission of the German Research Society, Verlag Chemie, Weinheim, 1984, p. 81 to 106. These dyes are usually used in concentrations of from 0.001 to 0.1% by weight, based on the total mixture.

Biogenic active ingredients are understood as meaning, for example, tocopherol, tocopherol acetate, tocopherol palmitate, ascorbic acid, deoxyribonucleic acid, coenzyme A10, retinol, bisabolol, allantoin, phytantriol, panthenol, AH acids, amino acids, hyaluronic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolysates, plant extracts and vitamin complexes.

The following examples are provided to illustrate some embodiments of the present invention and, as such, the present invention is not limited by these examples.

SYNTHESIS EXAMPLES

Example 1

The polyglycerol ester was prepared in 2 stages, which proceed in a manner known per se. Firstly, polyglycerol was esterified with fatty acid. 94.8 g (0.33 mol) of isostearic acid and 17.4 g (0.086 mol) of sebacic acid were esterified with 67.6 g of polyglycerol in the first stage at 240° C. while passing nitrogen through. The polyglycerol was characterized by its hydroxyl number of 1080. After a reaction time of 2 hours at this temperature, the acid number was <10. Then, at 240° C., 120 g of polyricinoleic acid were added while passing nitrogen through. The polyricinoleic acid was characterized by its acid number. It was between 100 and 30, preferably between 60 and 40. The mixture was then stirred at 240° C. until the AN was <5.

Example 2

The polyglycerol ester was prepared in 2 stages, which proceed in a manner known per se. Firstly, polyglycerol was esterified with fatty acid. 103.8 g (0.36 mol) of isostearic acid and 17.4 g (0.086 mol) of sebacic acid were esterified with 67.6 g of polyglycerol in the first stage at 240° C. while passing nitrogen through. The polyglycerol was characterized by its hydroxyl number of 1080. After a reaction time of 2 hours at this temperature, the acid number was <10. Then, at 240° C., 111 g of polyricinoleic acid were added while passing nitrogen through. The polyricinoleic acid was characterized by its acid number. It was between 100 and 30, preferably between 60 and 40. The mixture was then stirred at 240° C. until the AN was <5.

Example 3

The polyglycerol ester was prepared in 2 stages, which proceed in a manner known per se. Firstly, polyglycerol was esterified with fatty acid. 94.8 g (0.33 mol) of isostearic acid and 17.4 g (0.086 mol) of sebacic acid were esterified with 67.6 g of polyglycerol in the first stage at 240° C. while passing nitrogen through. The polyglycerol was characterized by its hydroxyl number of 1080. After a reaction time of 2 hours at this temperature, the acid number was <10. Then, at 240° C., 96 g of polyricinoleic acid were added while passing nitrogen through. The polyricinoleic acid was characterized by its acid number. It was between 100 and 30, preferably between 60 and 40. The mixture was then stirred at 240° C. until the AN was <5.

Example 4

The polyglycerol ester was prepared in 2 stages, which proceed in a manner known per se. Firstly, polyglycerol was esterified with fatty acid. 120 g (0.42 mol) of isostearic acid and 17.4 g (0.086 mol) of sebacic acid were esterified with 67.6 g of polyglycerol in the first stage at 240° C. while passing nitrogen through. The polyglycerol was characterized by its hydroxyl number of 1080. After a reaction time of 2 hours at this temperature, the acid number was <10. Then, at 240° C., 94.8 g of polyricinoleic acid were added while passing nitrogen through. The polyricinoleic acid was characterized by its acid number. It was between 100 and 30, preferably between 60 and 40. The mixture was then stirred at 240° C. until the AN was <5.

Example 5

The polyglycerol ester was prepared in 2 stages, which proceed in a manner known per se. Firstly, polyglycerol was esterified with fatty acid. 94.8 g (0.33 mol) of isostearic acid and 17.4 g (0.086 mol) of sebacic acid were esterified with 67.6 g of polyglycerol in the first stage at 240° C. while passing nitrogen through. The polyglycerol was characterized by its hydroxyl number of 1140. After a reaction time of 2 hours at this temperature, the acid number was <10. Then, at 240° C., 120 g of polyricinoleic acid were added while passing nitrogen through. The polyricinoleic acid was characterized by its acid number. It was between 100 and 30, preferably between 60 and 40. The mixture was then stirred at 240° C. until the AN was <5.

Example 6

The polyglycerol ester was prepared in 2 stages, which proceed in a manner known per se. Firstly, polyglycerol was esterified with fatty acid. 94.8 g (0.33 mol) of isostearic acid and 17.4 g (0.086 mol) of sebacic acid were esterified with 67.6 g of polyglycerol in the first stage at 240° C. while passing nitrogen through. The polyglycerol was characterized by its hydroxyl number of 850. After a reaction time of 2 hours at this temperature, the acid number was <10. Then, at 240° C., 120 g of polyricinoleic acid were added while passing nitrogen through. The polyricinoleic acid was characterized by its acid number. It was between 100 and 30, preferably between 60 and 40. The mixture was then stirred at 240° C. until the AN was <5.

Example 7

The polyglycerol ester was prepared in 2 stages, which proceed in a manner known per se. Firstly, polyglycerol was esterified with fatty acid. 103.8 g (0.36 mol) of isostearic acid and 17.4 g (0.086 mol) of sebacic acid were esterified with 67.6 g of polyglycerol in the first stage at 240° C. while passing nitrogen through. The polyglycerol was characterized by its hydroxyl number of 1080. After a reaction time of 2 hours at this temperature, the acid number was <10. Then, at 240° C., 90 g of polyricinoleic acid and 22 g of polyhydroxystearic acid were added while passing nitrogen through. The polyricinoleic acid was characterized by its acid number. It is between 100 and 30, preferably between 60 and 40. The mixture was then stirred at 240° C. until the AN was <5.

APPLICATION EXAMPLES

The following example emulsions were intended to illustrate the subject-matter of the invention in more detail without limiting it to these examples.

The concentration data in all of the examples is given as percent by weight.

Unless noted otherwise, the emulsions were prepared by firstly heating the oil phases to 80° C. The water phase was then stirred into the oil phase in about 5 to 10 minutes. When the stirring-in was complete, the mixture was briefly homogenized. If the W/O emulsions had been cooled to below 30° C., the mixture was homogenized a second time.

Emulsions 1 to 6

The emulsions 1 to 6 were intended to show, in particular, that by using the polyglycerol partial esters according to the present invention it was possible to obtain lotions with a significantly lower viscosity than can be obtained using PEG-free W/O emulsifiers currently available on the market.

As examples of emulsifiers customary for the prior art polyglyceryl-3 polyricinoleate and polyglyceryl-2 dipolyhydroxystearate were used.

|   |   | Emulsions | | |
|---|---|---|---|---|
|   |   | 1 % | 2 % | 3 % |
| A | Polyglycerol partial ester from Ex. 1 | 2.00 | | |
|   | Polyglyceryl-3 polyricinoleate | | 2.00 | |
|   | Polyglyceryl-2 dipolyhydroxystearate | | | 2.00 |
|   | Hydrogenated castor oil | 0.10 | 0.10 | 0.10 |
|   | Microcrystalline wax | 0.10 | 0.10 | 0.10 |
|   | Paraffinum perliquidum | 9.40 | 9.40 | 9.40 |
|   | Ethylhexyl palmitate | 9.40 | 9.40 | 9.40 |
| B | Glycerol | 3.00 | 3.00 | 3.00 |
|   | $MgSO_4 \cdot 7H_2O$ | 1.50 | 1.50 | 1.50 |
|   | Bronopol | 0.05 | 0.05 | 0.05 |
|   | Water | ad 100 | ad 100 | ad 100 |
|   | Stability | stable | stable | −15° C.** |
|   | Viscosity* [Pas] | 14 | 28 | 31 |

*Brookfield RVT Spindel 5, 10 rpm
**Water separation with two freeze-thaw cycles 25° C./−15° C.

|   |   | Emulsions | | |
|---|---|---|---|---|
|   |   | 4 % | 5 % | 6 % |
| A | Polyglycerol partial ester from Ex. 1 | 2.00 | | |
|   | Polyglyceryl-3 polyricinoleate | | 2.00 | |
|   | Polyglyceryl-2 dipolyhydroxystearate | | | 2.00 |
|   | Hydrogenated castor oil | 0.10 | 0.10 | 0.10 |
|   | Microcrystalline wax | 0.10 | 0.10 | 0.10 |
|   | Ethylhexyl palmitate | 9.40 | 9.40 | 9.40 |
|   | Caprylic/capric triglycerides | 9.40 | 9.40 | 9.40 |
| B | Glycerol | 3.00 | 3.00 | 3.00 |
|   | $MgSO_4 \cdot 7H_2O$ | 1.50 | 1.50 | 1.50 |
|   | Bronopol | 0.05 | 0.05 | 0.05 |
|   | Water | ad 100 | ad 100 | ad 100 |
|   | Stability | stable | stable | −15° C.** |
|   | Viscosity* [Pas] | 21 | 36 | 32 |

*Brookfield RVT Spindel 5, 10 rpm
**Water separation with two freeze-thaw cycles 25° C./−15° C.

The example emulsions clearly showed by using different oil phases, that a polyglycerol partial ester according to the present invention lead to significantly lower emulsion viscosities than was possible with PEG-free W/O emulsifiers customary for the prior art.

At the same time, the emulsions prepared using the polyglycerol partial ester according to the present invention from Example 1 exhibited an excellent light feel on the skin.

Besides an excellent thermal and viscosity stability, the polyglycerol partial ester according to the present invention from Example 1 was also characterized by an excellent low-temperature stability of the emulsions.

Emulsions 7 to 10

The emulsions 7 to 10 were intended to show, in particular, that by using the polyglycerol partial esters according to the present invention it is possible to obtain stable low-viscosity W/O emulsions with a large number of different oils. Example emulsion 10, in particular, which comprises relatively large amounts of cyclopentasiloxane, was characterized by an excellent light feel on the skin.

|   |   | Emulsions | | | |
|---|---|---|---|---|---|
|   |   | 7 % | 8 % | 9 % | 10 % |
| A | Polyglycerol partial ester from Ex. 2 | 2.50 | 2.50 | 2.00 | 2.00 |
|   | Hydrogenated castor oil | 0.25 | 0.25 | 0.25 | 0.10 |
|   | Microcrystalline wax | 0.25 | 0.25 | 0.25 | 0.10 |
|   | Isohexadecane | 5.00 | | | |
|   | Cetearyl ethylhexanoate | 5.00 | 7.00 | | |
|   | Ethylhexyl stearate | 7.00 | | | |
|   | Diethylhexyl carbonate | | 8.00 | 8.50 | 8.90 |
|   | Jojoba oil | | 4.00 | | |
|   | Triisostearin | | | 3.00 | |
|   | Paraffinum perliquidum | | | 10.0 | |
|   | Cylcopentasiloxane | | | | 8.90 |
| B | Glycerol | 3.00 | 3.00 | 3.00 | 3.00 |
|   | $MgSO_4 \cdot 7H_2O$ | 1.50 | 1.50 | 1.50 | 1.50 |
|   | Panthenol | 0.50 | 0.50 | 0.50 | |
|   | Bronopol | 0.05 | 0.05 | 0.05 | 0.05 |
|   | Ethanol | 3.00 | | | |
|   | Water | ad 100 | ad 100 | ad 100 | ad 100 |
|   | Stability | stable | stable | stable | stable |
|   | Viscosity* | 17 | 15 | 12 | 11 |

*Brookfield RVT Spindel 5, 10 rpm

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A polyglycerol partial ester of polyricinoleic acid and sebacic acid, prepared by esterification of a polyglycerol mixture with components comprising:
   (i) at least one polyricinoleic acid of the general formula 1

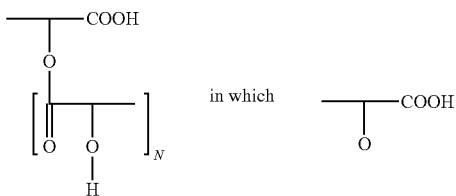

is a hydroxy fatty acid group selected from ricinoleic acid and hydroxystearic acid groups, provided that at least a portion of the hydroxy fatty acid groups includes one or more ricinoleic acid groups, wherein N is a number from 1 to 10; and
   (ii) sebacic acid;
wherein said polyglycerol mixture has a homolog distribution in which glycerol is in an amount of less than 5% by weight of the polyglycerol mixture.

2. The polyglycerol partial ester of claim 1, wherein the polyglycerol mixture has an average degree of condensation of from 1 to 11.

3. The polyglycerol partial ester of claim 1, wherein the polyricinoleic acid has an average degree of condensation of from 1 to 10.

4. The polyglycerol partial ester of claim 1, wherein between 20 and 75% of the OH groups of the polyglycerol mixture are esterified.

5. The polyglycerol partial ester of claim 1, prepared by esterification of
   a) 1.0 mol of OH groups of the polyglycerol mixture with
   b) 0.01 to 0.5 mol of COOH groups of the polyricinoleic acid and
   c) 0.01 to 0.5 mol of COOH groups of said sebacic acid,
   with the proviso that the sum of the COOH groups corresponds to about 20 to 75% of the OH groups of the polyglycerol mixture.

6. A cosmetic, dermatological or pharmaceutical preparation which comprises at least one of the polyglycerol partial esters as claimed in claim 1, and optionally, one or more of auxiliaries and/or additives.

7. A care and cleaning composition for household and industrial applications which comprises at least one of the polyglycerol partial esters as claimed in claim 1, and optionally, one or more of auxiliaries and/or additives.

8. The polyglycerol partial ester of claim 1, further comprising a polyhydroxystearic acid.

9. The polyglycerol partial ester of claim 1, wherein said sebacic acid is in an amount of up to 6.3% by weight of the total weight of the polyglycerol partial ester composition.

* * * * *